United States Patent
Hayashi et al.

(10) Patent No.: US 6,515,743 B1
(45) Date of Patent: Feb. 4, 2003

(54) SCANNER-TYPE FLUORESCENCE DETECTION APPARATUS USING SMALL SIZED EXCITATION LIGHT SOURCE

(75) Inventors: Toshinori Hayashi, Kanagawa (JP); Yoshifumi Kurihara, Kanagawa (JP); Takahiko Ishiguro, Kanagawa (JP)

(73) Assignee: Tosoh Corporation, Yamaguchi (JP)

( * ) Notice: Subject to any disclaimer, the term of this patent is extended or adjusted under 35 U.S.C. 154(b) by 222 days.

(21) Appl. No.: 09/667,722

(22) Filed: Sep. 22, 2000

(30) Foreign Application Priority Data

Sep. 22, 1999  (JP) .......................................... 11-268893

(51) Int. Cl.⁷ .............................................. G01N 21/64
(52) U.S. Cl. ........................ 356/317; 356/318; 356/417; 250/458.1
(58) Field of Search .................................. 356/317, 318, 356/417; 250/458.1, 459.1, 461.1, 461.2

(56) References Cited

U.S. PATENT DOCUMENTS 4,406,547 A    9/1983   Aihara
5,178,833 A    1/1993   Covain

FOREIGN PATENT DOCUMENTS

| EP | 0 985 927 A2 | 3/2000 |
| EP | 1 024 355 A1 | 8/2000 |
| GB | 2 000 284 A | 1/1979 |
| JP | 2000-88752 | 3/2000 | .......... G01N/21/64 |

Primary Examiner—F. L. Evans
(74) Attorney, Agent, or Firm—Sughrue Mion, PLLC

(57) ABSTRACT

A fluorescence detection apparatus comprising: a sample holder for fixing and holding sample vessels on a circular arc; a partition plate being joined to drive means for rotation on the center of the circular arc; an excitation light source; excitation light optical means; and fluorescence optical means containing a light guide being fixed on the partition plate for rotation integrally and a photosensor. The photosensor is mechanically discontinued from the drive means and fixedly placed. The fluorescence signal emission end of the light guide is placed facing the photosensor on the rotation center axis and the partition plate and the parts fixed thereto are rotated integrally, whereby fluorescence detection of the samples arranged on the circular arc is repeated in order.

8 Claims, 10 Drawing Sheets

HEAT INSULATION MATERIAL

SCANNER-TYPE FLUORESCENCE DETECTION APPARATUS USING SMALL SIZED EXCITATION LIGHT SOURCE

BACKGROUND OF THE INVENTION

1. Field of the Invention

This invention relates to a fluorescence detection apparatus for detecting a fluorescence signal from a specific substance contained in a sample and quantifying the specific substance from the detected fluorescence signal amount and in particular to a fluorescence detection apparatus useful for monitoring a large number of samples in real time (tracing change of the fluorescence signal amount with time) in a clinical diagnosis field requiring incubation at a predetermined temperature, such as an enzyme reaction.

2. Description of the Related Art

To monitor producing a fluorescent reaction product by an enzyme reaction in real time, etc., it is necessary to detect fluorescence while incubating a sample (reaction liquid) at a predetermined temperature. Moreover, a large number of samples need also to be treated promptly at the same time in fields of clinical diagnosis, etc.

A first method used in the conventional clinical diagnosis field, etc., is a method of detecting fluorescence in order while transporting samples along a temperature-adjusted guide. For example, the temperature of a guide manufactured with a material having good thermal conductivity such as an aluminum alloy is adjusted by a heater, etc., samples placed in a holder are transported along the guide using a chain, a turn table, or the like one or more than one at a time, and a fluorescence signal is detected in order by a fluorescence detector placed along the guide.

In addition, a second method of detecting fluorescence at the same time about a large number of samples, for example, by placing a joint-type sample vessel, titer plate, etc., capable of storing a large number of samples on temperature adjustment means is also known. A fluorescence detection apparatus used for the purpose comprises (a) a plurality of photosensors or (b) a multichannel-type photosensor or has (c) mechanical move means for moving photosensor or light guide (means for guiding a fluorescence signal emitted from a sample vessel to photosensor, such as an optical fiber).

The apparatus (a) is a fluorescence detection apparatus for using as many photosensors as samples for detecting fluorescence at the same time to detect a fluorescence signal separately from each sample. In such an apparatus, it is common practice to use a light guide for dividing excitation light from a light source and guiding to each sample.

The apparatus (b) is a fluorescence detection apparatus for using an image sensor such as CCD or a photodiode array in place of a plurality of photosensors, thereby detecting fluorescence signals from aligned samples as an image in a state in which the positional relationship between light emission points is held. In such an apparatus, it is also common practice to guide excitation light from a light source to each sample by using a division-type light guide, such as an optical device or an optical fiber.

In the apparatus (c), the photosensor is moved mechanically on a large number of samples or samples are moved to the fluorescence detection position of the photosensor in order; most used is a configuration of moving the light guide mechanically. In this configuration, an excitation light guide and a fluorescence light guide are used and the ends of both guides placed on the sample side are made integral with each other, then both guides are moved at the same time, whereby fluorescence is detected while a large number of samples are excited in order.

To use the fluorescence detection apparatus in the conventional arts to monitor change of a fluorescence signal with time from a specific substance contained in a sample in real time while incubating the sample at a predetermined temperature, the following problems are involved:

The first method described above involves the risk of insufficient temperature adjustment accuracy, the limit of the number of treated samples, carry-over, etc., because samples are transported along the temperature-adjusted guide and fluorescence is detected in order. That is, it is difficult to adjust the whole sample transport guide at a uniform temperature and hold the thermal conductivity between the transport guide and each sample constant over the whole guide; consequently, temperature change of the sample may occur during transporting or the samples may differ in temperature. Since fluorescence is detected about the transported samples one at a time, the same sample must be transported repeatedly to monitor change of a fluorescence signal with time for a long time, thus the number of samples that can be treated is limited. Further, the risk of contamination (carry-over) between the samples caused by a sample splash cannot be excluded.

The second method described above can solve the problems of the first method, but may introduce the following new problems:

First, the conventional apparatus (a) comprises a plurality of photosensors, thus the manufacturing costs are increased and the space matching the number of photosensors also becomes necessary. If an attempt is made to miniaturize the apparatus, several photosensors can only be installed because of the limit of the space; after all, the number of samples that can be treated at the same time is only a few. Although use of small-sized photosensors such as photodiodes can also be considered, there is a problem of insufficient sensitivity to feeble fluorescence, and it becomes necessary to correct the sensitivity of each photodiode. Further, the strength of a fluorescence signal is proportional to the excitation light strength and thus if excitation light from the light source is divided, detection sensitivity is worsened; this is also a problem.

Next, the apparatus (b) has insufficient sensitivity to feeble fluorescence and thus is not adequate. To augment insufficient sensitivity, an element for amplifying the light quantity via electron amplification by a microchannel plate (so-called image intensifier) or the like may be used in combination, but is used only in special research application under the present circumstances because of an extremely rise in costs. Since fluorescence from a wide range is detected as an image, there are also problems of unevenness of light quantity detection caused by lens aberration and data processing load caused by an enormous data amount.

With the apparatus (c), the move range is limited because of the limit of the bendability of the light guide and moreover there is a possibility of breaking light guide. Since light communication efficiency is changed because the light guide is bent, it is difficult to make fluorescence detection good in reproducibility. On the other hand, a mechanical move of the photosensor also involves a move of attached cables, etc., thus the move range is limited and there is a possibility of breaking the cable, etc.

In addition, scanner-type fluorescence detection apparatus as disclosed in Japanese patent Unexamined Publication No. 2000-088752 (P2000-88752A) and an apparatus as shown in FIG. 6 invented as means for solving problems of the above-described apparatus are also available. The scanner-type fluorescence detection apparatus described in Japanese patent Unexamined Publication No. 2000-088752 is as follows: As shown in FIGS. 5A AND 5B, sample vessels are arranged like a circular arc and a ring section of a ring-type light guide 21 is placed closely facing the sample vessels with putting a partition plate 23 therebetween and excitation light optical means 25 and fluorescence optical means 26 are fixed to the partition plate for rotation integrally, whereby separately gathered fluorescence signals are communicated through the ring-type light guide 21 to a photosensor 22. In the scanner-type fluorescence detection apparatus as shown in FIG. 6A and 6B, sample vessels are arranged like a plurality of circular arcs and a ring-type light guide 31 is placed facing the sample vessels with a partition plate 33 between and excitation light optical means 35 and fluorescence optical means 36 containing at least one light guide are fixed to the partition plate 33 for rotation integrally, whereby separately gathered fluorescence signals are communicated through the ring-type light guide 31 to a photosensor 32.

The scanner-type fluorescence detection apparatus as shown in FIGS. 5A, 5B, 6A and 6B, can solve the conventional problem. However, if a small-sized and low-output excitation light source is used to furthermore miniaturize the whole apparatus, the fluorescence signal becomes extremely feeble and even if a high-sensitivity photosensor such as a photomultiplier tube is used, insufficient sensitivity may result, because the incidence port of the ring-type light guide (21, 31) used for communicating the fluorescence signal generally is narrow as several hundred $\mu$m and the fluorescence signal communication efficiency is low. Particularly, in the scanner-type fluorescence detection apparatus as shown in FIGS. 6A and 6B, the second light guide which rotates is placed in series in addition to the ring-type light guide 31 placed still and a signal is communicated therebetween, thus the scanner-type fluorescence detection apparatus easily falls into insufficient sensitivity to extremely feeble fluorescence. If a high-output excitation light source such as an argon ion laser is used, the problem of insufficient sensitivity is resolved, but a large space is required for the excitation light source together with a control power supply, presenting an obstacle to miniaturization of the apparatus.

Thus, the fluorescence detection apparatus for monitoring a fluorescence signal in real time, particularly for monitoring a fluorescence signal in real time while incubating a sample at a predetermined temperature need satisfy the requirements of (a) high-accuracy temperature adjustment, (b) rapid treatment of a large number of samples, (c) high sensitivity, (d) high reliability (decrease in mechanical trouble typified by broken line, moving part operation failure, etc., improvement in reproducibility of fluorescence detection, decrease in the risk of carry-over), (e) low costs (simplification of apparatus configuration, use of no expensive parts in data processing, etc.,), (f) miniaturization of the apparatus, and the like.

SUMMARY OF THE INVENTION

It is therefore an object of the invention to provide a fluorescence detection apparatus satisfying the requirements and in particular to a fluorescence detection apparatus using a small-sized and high-sensitivity optical system of fluorescence analysis, useful for monitoring a large number of fixed samples in real time and a fluorescence detection apparatus provided with an incubation function of temperature control means.

To the end, according to a first aspect of the invention, there is provided a fluorescence detection apparatus comprising a sample holder for fixing and holding sample vessels on a circular arc, a partition plate being joined to drive means for rotation on the center of the circular arc, an excitation light source, excitation light optical means, and fluorescence optical means being fixed on the partition plate for rotation integrally, and a photosensor being mechanically discontinued from the drive means and fixedly placed. In the fluorescence detection apparatus, (a) the excitation light optical means is placed so as to guide excitation light from the excitation light source from the rotation center side of the partition plate and selectively excite one of the sample vessels, (b) the fluorescence optical means contains a light guide for communicating a fluorescence signal from the sample vessel to the photosensor and an incidence end of the light guide is placed so as to be able to face the sample vessel with the partition plate between so that the fluorescence signal can be gathered and an emission end of the light guide is placed so as to be able to face the photosensor on the rotation center axis of the partition plate, and (c) while the excitation light is guided to the sample vessels placed on the circular arc in order as the partition plate is rotated, fluorescence is detected through the fluorescence optical means containing the light guide at the same time.

To the end, according to a second aspect of the present invention, the fluorescence detection apparatus as shown in the first aspect further includes wavelength dispersion means facing the emission end of the light guide for dispersing fluorescence into optical paths depending on the wavelength of the fluorescence signal, wherein a photosensor is fixedly placed on each of the optical paths, whereby fluorescence signals having a plurality of wavelengths can be detected at the same time.

To the end, according to a third aspect of the present invention, the fluorescence detection apparatus as shown in the first or second aspect further includes a shading plate for covering at least the top of one sample vessel, the shading plate being fixed to the partition plate so as to be positioned above the fluorescence incidence end of the light guide forming a part of the fluorescence optical means. Then the shading plate is rotated with the partition plate integrally, thereby shielding at least the sample vessel under fluorescence measurement in order from extraneous light.

To the end, according to a fourth aspect of the present invention, in the fluorescence detection apparatus as shown in the first, second or third aspect, a light emitting diode or a semiconductor laser is used as the excitation light source.

To the end, according to a fifth aspect of the present invention, in the fluorescence detection apparatus as shown in the first, second, or third aspect, the light guide being one component of the fluorescence optical means is one optical fiber.

To the end, according to a sixth aspect of the present invention, in the fluorescence detection apparatus as shown in the second or third aspect, the wavelength dispersion means for dispersing fluorescence into optical paths depending on the wavelength of the fluorescence signal is a dichroic mirror.

To the end, according to a seventh aspect of the present invention, the fluorescence detection apparatus as shown in the first, second, or third aspect further includes temperature adjustment means for controlling each sample at a predetermined temperature.

DETAILED DESCRIPTION OF THE PREFERED EMBODIMENT

A fluorescence detection apparatus of the invention will be discussed in detail with reference to the accompanying drawings.

Figure 1A:
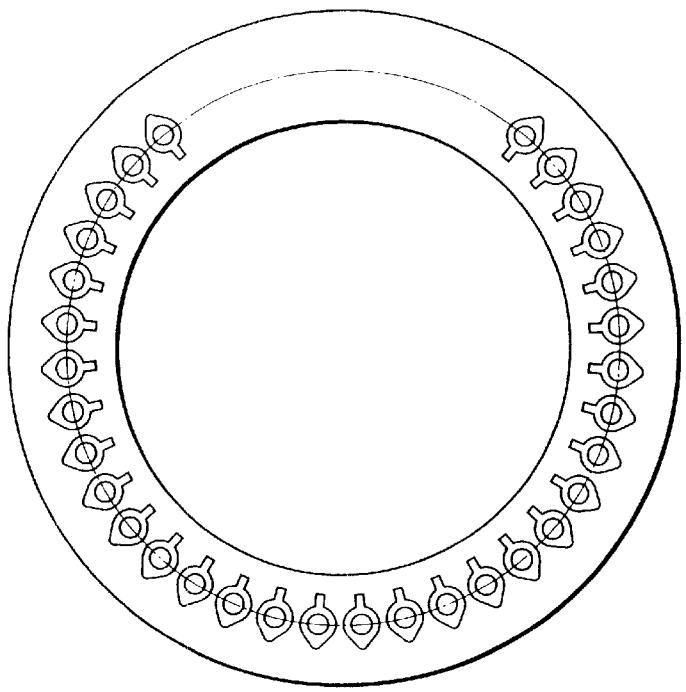
FIGS. 1A and 1B are drawings to show an outline of a fluorescence detection apparatus of the invention.
Figure 1B:
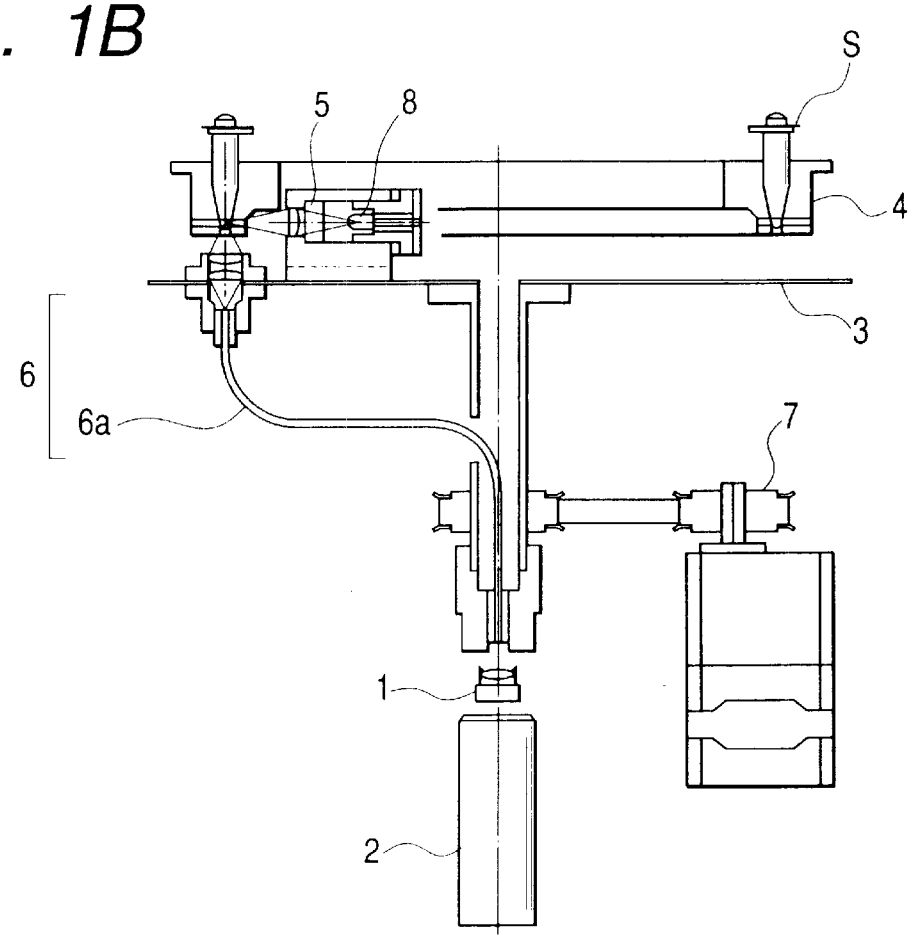

FIGS. 1A and 1B show an outline of a first embodiment of the present invention, a fluorescence detection apparatus using a small-sized and high-sensitivity optical system of fluorescence analysis, useful for monitoring a large number of fixed samples in real time.

A sample holder (4) comprises hold holes fitted to the outer shape of each sample vessel S on a circular arc for fixedly holding the sample vessels (S) each storing a sample on the circular arcs. Placement of the sample vessels (S) on the circular arcs is not limited to the placement of the sample vessels (S) equally spaced from each other as shown in the figure and may be placement of the sample vessels (S) unequally spaced from each other. The number of sample vessels fixedly held in the sample holder (4) is not limited and may be determined from the length of each circular arc, the outer diameter of each sample vessel, etc. Further, the shape of the top of the sample holder (4) is not limited to a circle and can also be made a polygon such as a quadrangle.

The sample vessel may be any if it is made of a material capable of allowing excitation light and fluorescence to pass through and chemically stable toward the stored sample; it can be appropriately selected and used considering the sample amount, etc., presented for fluorescence detection. Particularly, to monitor reaction while amplifying a nucleic acid as an enzyme in so-called PCR, NASBA, etc., preferably a sample vessel (S) having a sealing plug is used for the purpose of preventing the amplified nucleic acid from scattering.

Placed below the fixedly placed sample holder (4) is a partition plate (3) joined to drive means (7) for rotation on the center of the circular arc of each sample vessel (S) placed on the circular arc. Further, an excitation light source (8), excitation light optical means (5), and fluorescence optical means (6) are fixed to the partition plate (3) and these are rotated integrally by the action of the drive means (7).

Preferably, the partition plate (3) is implemented as a disk for stabilizing rotation. It has a size (radius) made larger than at least the distance between the circular arc center and the sample vessel (S) so as to cut off the fluorescence optical path from the sample vessel to a photosensor (2) except for the location where the fluorescence optical means (6) described later exists. However, a circular or slit-like hole is made only in the location where the fluorescence optical means (6) described later is fixed so as to allow a fluorescence signal to pass through. The partition plate (3) can also be placed above the sample vessels (S), but a device of detaching the partition plate (3) to place the sample vessels (S) in the sample holder (4) or the like becomes necessary. Further, the sample amount often is small as several ten μl, in which case the fluorescence detection efficiency is raised if a fluorescence signal is gathered from the bottom of the sample vessel (S). For these reasons, preferably the partition plate (3) is placed below the sample holder (4).

The excitation light source (8) may be selected considering the excitation wavelength of a sample; such an excitation light source providing a sufficient light quantity of excitation light arriving at one sample vessel through the excitation light optical means (5) is used. To fix the excitation light source (8) on the partition plate (3), preferably the excitation light source is small-sized as much as possible. More particularly, a light emitting diode or a semiconductor laser can be exemplified; a light emitting diode is used in the example in FIGS. 1A, B.

The excitation light optical means (5) fixed on the partition plate (3) is means for selecting the wavelength of excitation light from light of the excitation light source (8) and selectively guiding the excitation light into only one of the sample vessels placed like circular arcs. In the apparatus, optical means (1) comprising wavelength selection means and condensing means is provided. In the example in FIG. 1B, an interference filter is used as the wavelength selection means and light can be collected on a specific sample vessel through an optical lens. The expression "guiding the excitation light into only one of the sample vessels" is not used in a strict sense; it is enough to intentionally guide the excitation light into one of the sample vessels and, for example, if a very small amount of excitation light arrives at any other sample vessel by reflection on the outer wall of the one sample vessel, there is no harm.

The fluorescence optical means (6) fixed on the partition plate (3) contains at least one light guide (6a); it is means for communicating only fluorescence emitted from the sample vessel into which the excitation light is guided as described above to the photosensor (2). Therefore, a fluorescence incidence end and a fluorescence emission end of the light guide (6a) are placed facing the sample vessel and the photosensor (2), respectively. Of course, condensing means of an optical lens, etc., intended for improving the fluorescence communication efficiency or wavelength selection means for selecting fluorescence wavelength may be inserted between the sample vessel (S) and the fluorescence incidence end of the light guide (6a). The condensing means or the wavelength selection means may be inserted between the fluorescence signal emission end of the light guide (6a) and the photosensor (2). In the example in FIG. 1B, the condensing means is inserted between the sample vessel (S) and the fluorescence incidence end of the light guide (6a) and the condensing means and the wavelength selection means are inserted between the fluorescence signal emission end of the light guide (6a) and the photosensor (2).

The fluorescence signal emission end of the light guide (6a) is placed on the rotation center axis of the partition plate (3). Thus, if the partition plate (3) joined to the rotation drive mechanism (7) is rotated, the position of the fluorescence signal emission end of the light guide (6a) does not change and it is made possible to communicate a fluorescence signal to the photosensor (2) with the same efficiency. As the optimum light guide, one optical fiber rich in flexibility or a dense bundle of optical fibers whose end faces are aligned with a proper metal fixture at both ends can be used.

In the apparatus in FIGS. 1A and 1B adopting the described configuration, as the partition plate (3) is rotated, excitation light is guided by the excitation light optical means (5) into the sample vessels fixedly held in the sample holder (4) one at a time in order. At the same time, fluorescence emitted from the sample vessel (S) is detected by the photosensor (2) through the fluorescence optical means (6) containing the light guide (6a). Therefore, if the detection result of the photosensor (2) is stored while rotation of the partition plate (3) is controlled using a computer, etc., the intermittent fluorescence detection result of any desired sample held in the sample holder (4) can be provided and real-time monitoring can be accomplished.

Thus, the whole apparatus can be miniaturized by fixing the light source on the partition plate (3). Particularly, to use an external large-sized excitation light source such as an argon ion laser as in the scanner-type fluorescence detection apparatus as shown in FIG. 5A to FIG. 6B, the effect of miniaturizing the apparatus of the invention is very clear because a laser body tube and its control power supply occupy a large volume.

In the scanner-type fluorescence detection apparatus as shown in FIG. 5A to FIG. 6B, the rotation center axis of the partition plate (23, 33) overlaps the optical path of excitation light and therefore must be avoided as the communication optical path of a fluorescence signal and the ring-type light guide (21, 31) comprising optical fibers arranged like a ring at the fluorescence incidence end is used. Since the fluorescence signal incidence end of the ring-type light guide is narrow as several hundred μm, the incidence efficiency of a fluorescence signal is low and the fluorescence detection sensitivity may become insufficient. In the invention, however, the excitation light source is fixed on the partition plate (3), so that the rotation center axis of the partition plate (3) can be used to communicate the fluorescence signal and the ring-type light guide is not required as means for communicating the fluorescence signal and one light guide makes it possible to communicate the fluorescence signal with high efficiency. Thus, the advantage that high-sensitivity detection of the fluorescence signal can be accomplished can be provided.

Figure 2:
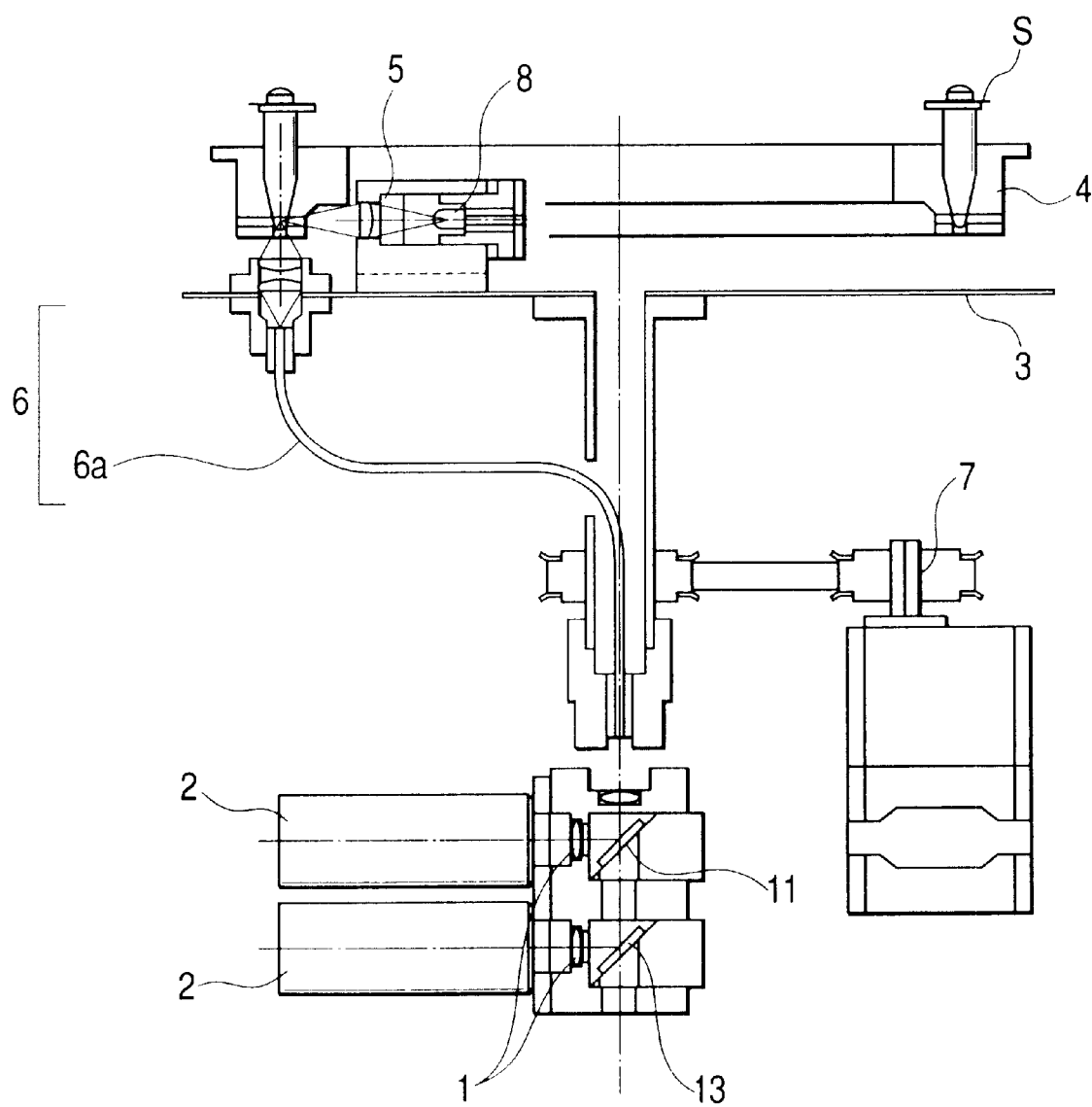
FIG. 2 is a drawing to show an outline of a fluorescence detection apparatus of the invention that can detect multiple wavelengths at the same time.

FIG. 2 shows an outline of a second embodiment of the present invention, a fluorescence detection apparatus that can detect fluorescence signals of different wavelengths at the same time, useful for monitoring a large number of fixed samples in real time.

Wavelength dispersion means (11) is an element for dispersing fluorescence emitted from a light guide (6a) into optical paths depending on the wavelength. In the embodiment, a dichroic mirror is used for separating a fluorescence signal into reflected light and transmitted light depending on the wavelength. The reflected light is detected by a photosensor through an optical means (1) (an interference filter and a condensing lens) and the transmitted light is detected by a photosensor (2) through a total reflection mirror (13), an interference filter, and a condensing lens. Of course, to detect the transmitted light, the total reflection mirror (13) can also be omitted. Further, for the reflected light or the transmitted light, another dichroic mirror is used in combination, whereby the number of dispersed wavelengths can also be increased. Thus, the fluorescence signals of different wavelengths can be detected at the same time.

Use of a diffraction grating is also possible as another wavelength dispersion element (11). Since the diffraction grating disperses wavelength continuously, if as many photosensors as required are placed in the travel direction of light of the target wavelength, multiple-wavelength fluorescence detection can be made. It is also made possible to measure a fluorescence spectrum by using CCD or a photodiode array, for example, as the photosensor.

Figure 3:
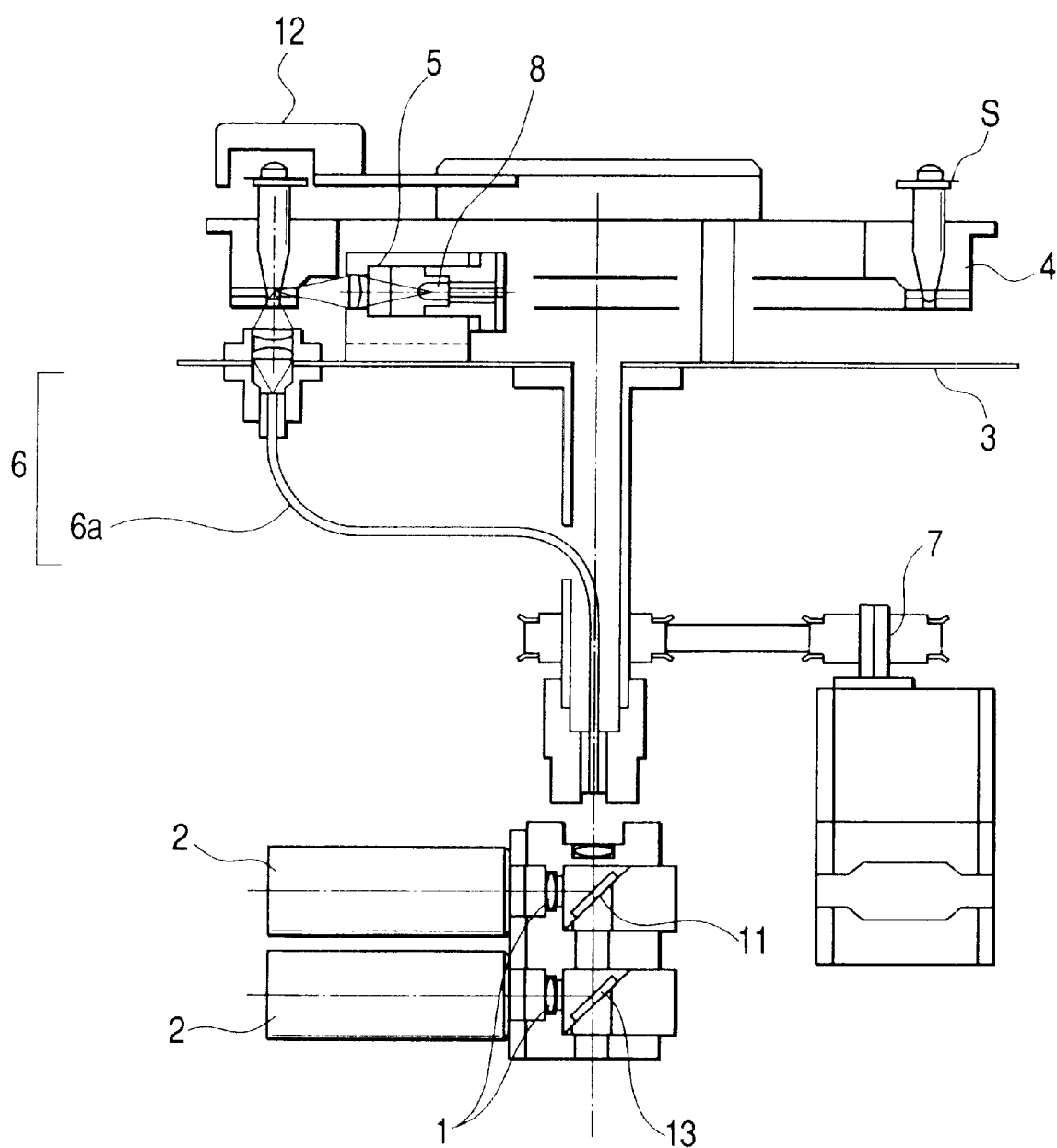
FIG. 3 is a drawing to show an outline of a fluorescence detection apparatus of the invention comprising a shading plate.

FIG. 3 shows an outline of a third embodiment of the present invention, a fluorescence detection apparatus that can prevent disturbance of extraneous light, useful for monitoring a large number of fixed samples in real time.

To detect a feeble fluorescence signal, it is important to exclude disturbance of extraneous light and a shading plate (12) is used for such a purpose. The shading plate (12) may be sized and shaped and have a surface color so that it can cover at least the top of one sample vessel (S) and prevent extraneous light from entering the vessel. Normally, preferably the surface color is black. The shading plate (12) is fixed to a partition plate (3) so as to be positioned above the fluorescence signal incidence end of a light guide (6a) forming a part of fluorescence optical means (6) for rotation integrally with rotation of the partition plate (3). Thus, extraneous light can be prevented from entering at least the sample vessel or fluorescence optical means (6) under fluorescence measurement and it is made possible to detect a fluorescence signal stably. Further, it is desirable that the shading plate is formed as like beach parasol as shown in FIG. 3.

Figure 4A:
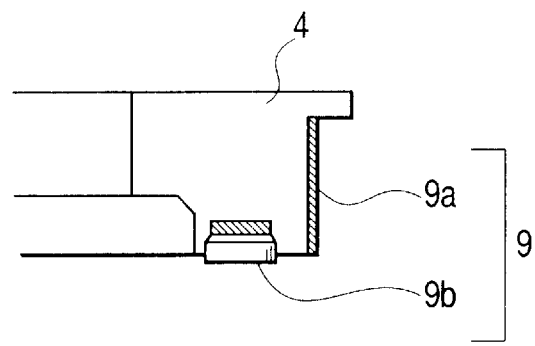
FIGS. 4A and 4B are drawings to show an outline of a fluorescence detection apparatus of the invention comprising temperature adjustment means.
Figure 4B:
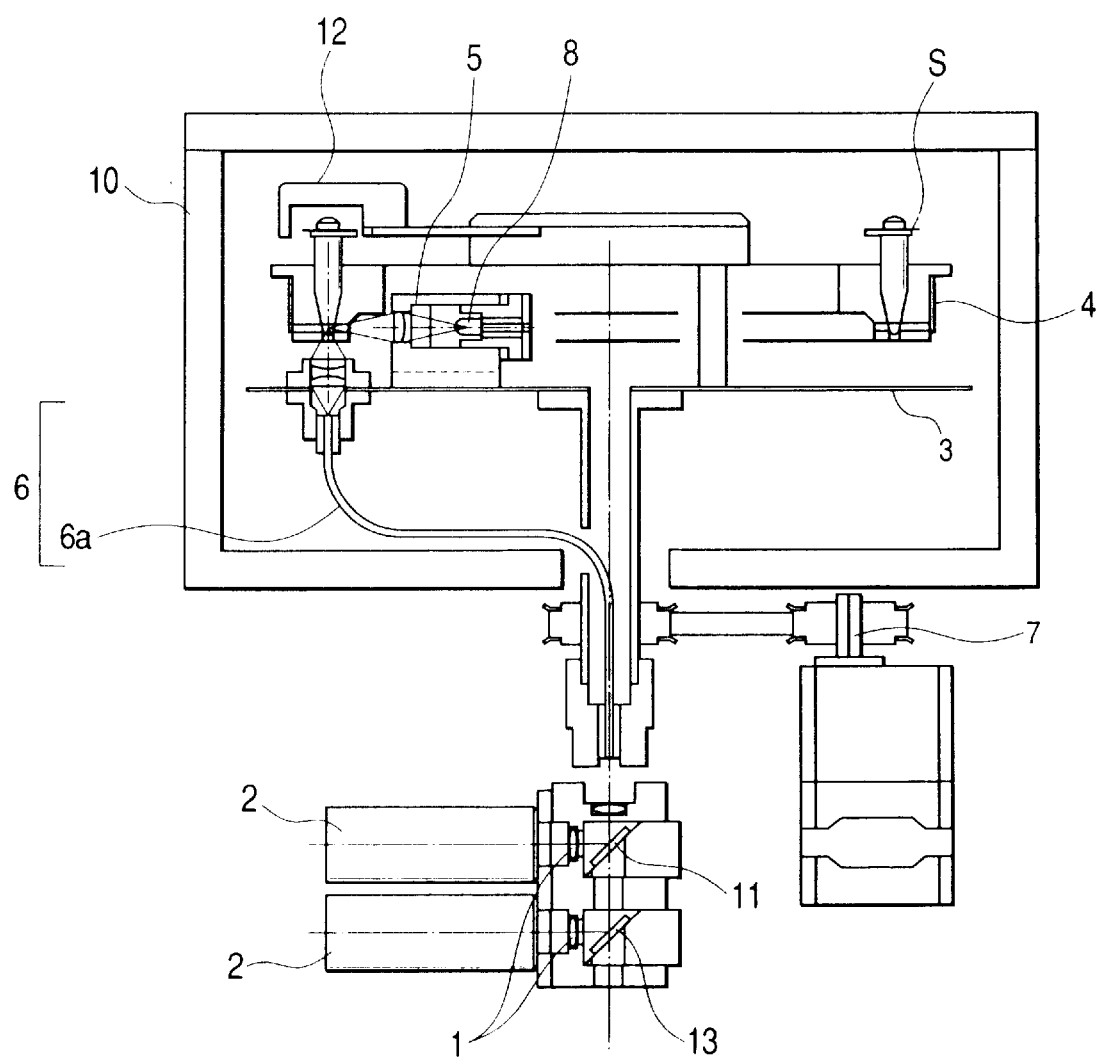
Figure 5A:
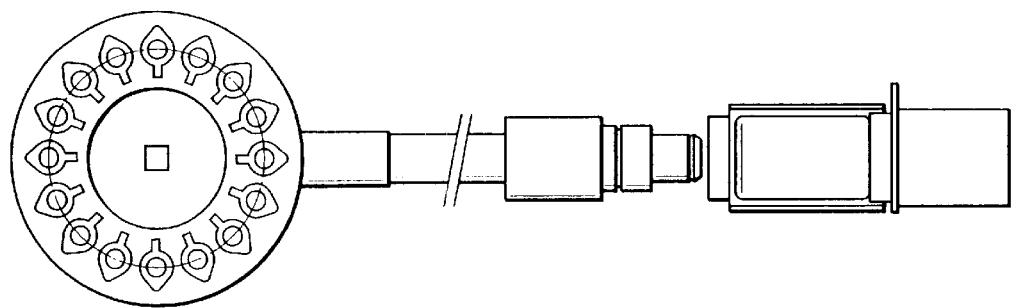
FIGS. 5A and 5B are a drawing to show an outline of a scanner-type fluorescence detection apparatus in a related art.
Figure 5B:
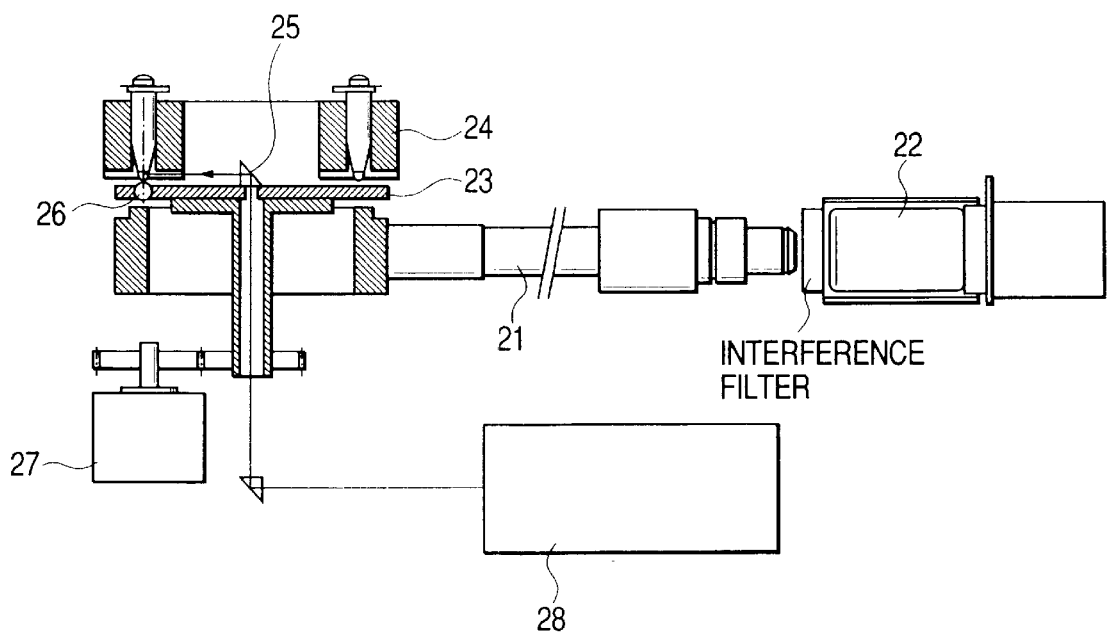
Figure 6A:
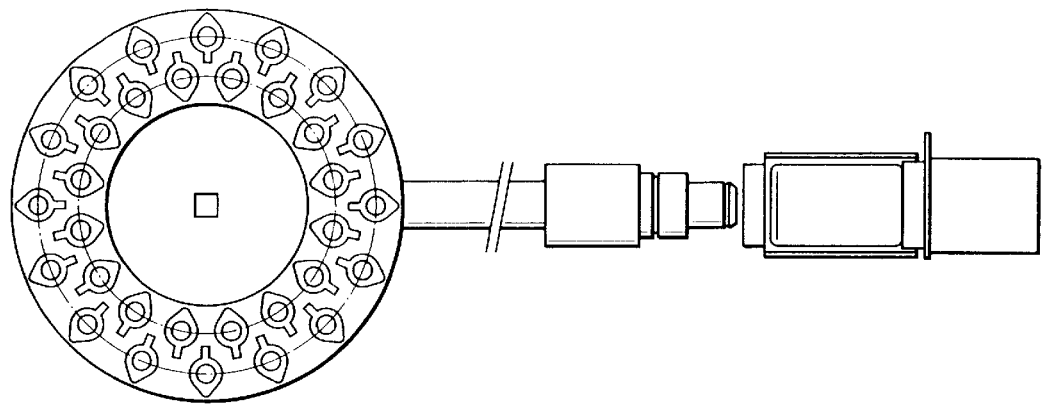
FIGS. 6A and 6B is a drawing to show an outline of a scanner-type fluorescence detection apparatus in a related art.
Figure 6B:
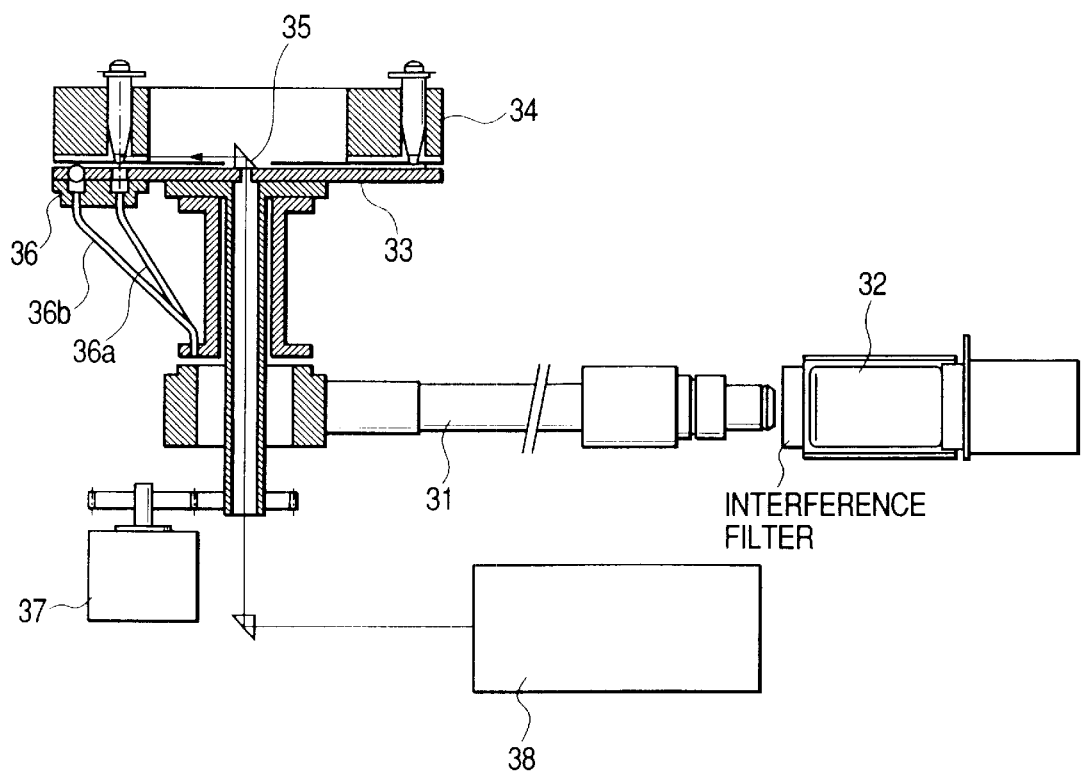
Figure 7A:
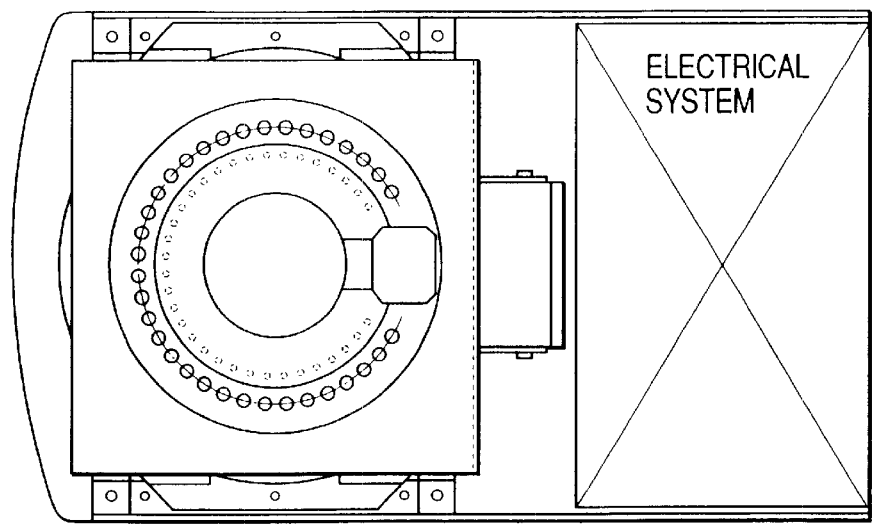
FIGS. 7A and 7B are general views to describe one embodiment of a fluorescence detector of the invention.
Figure 7B:
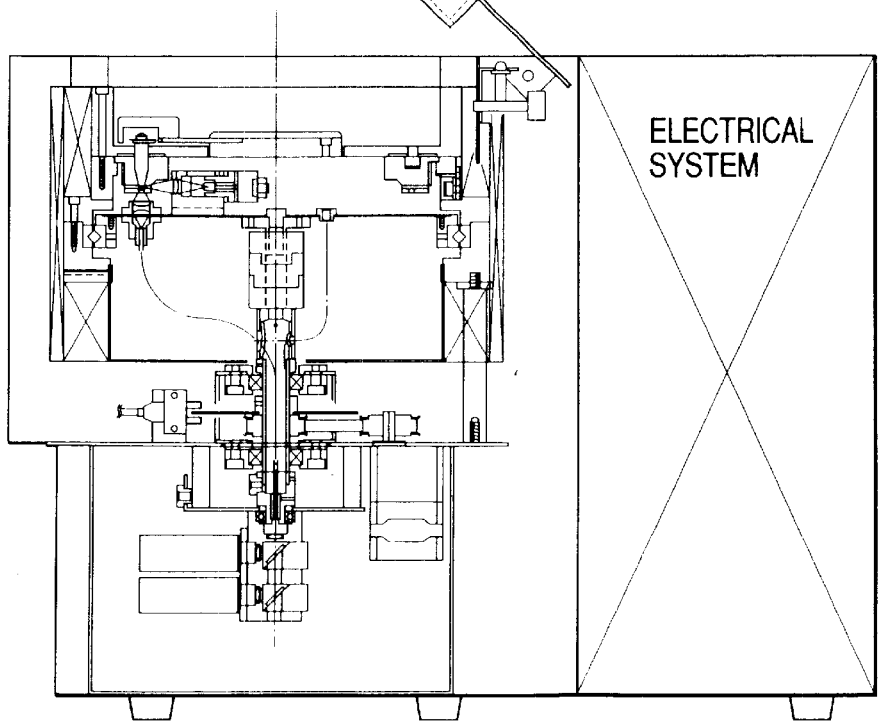
Figure 8:
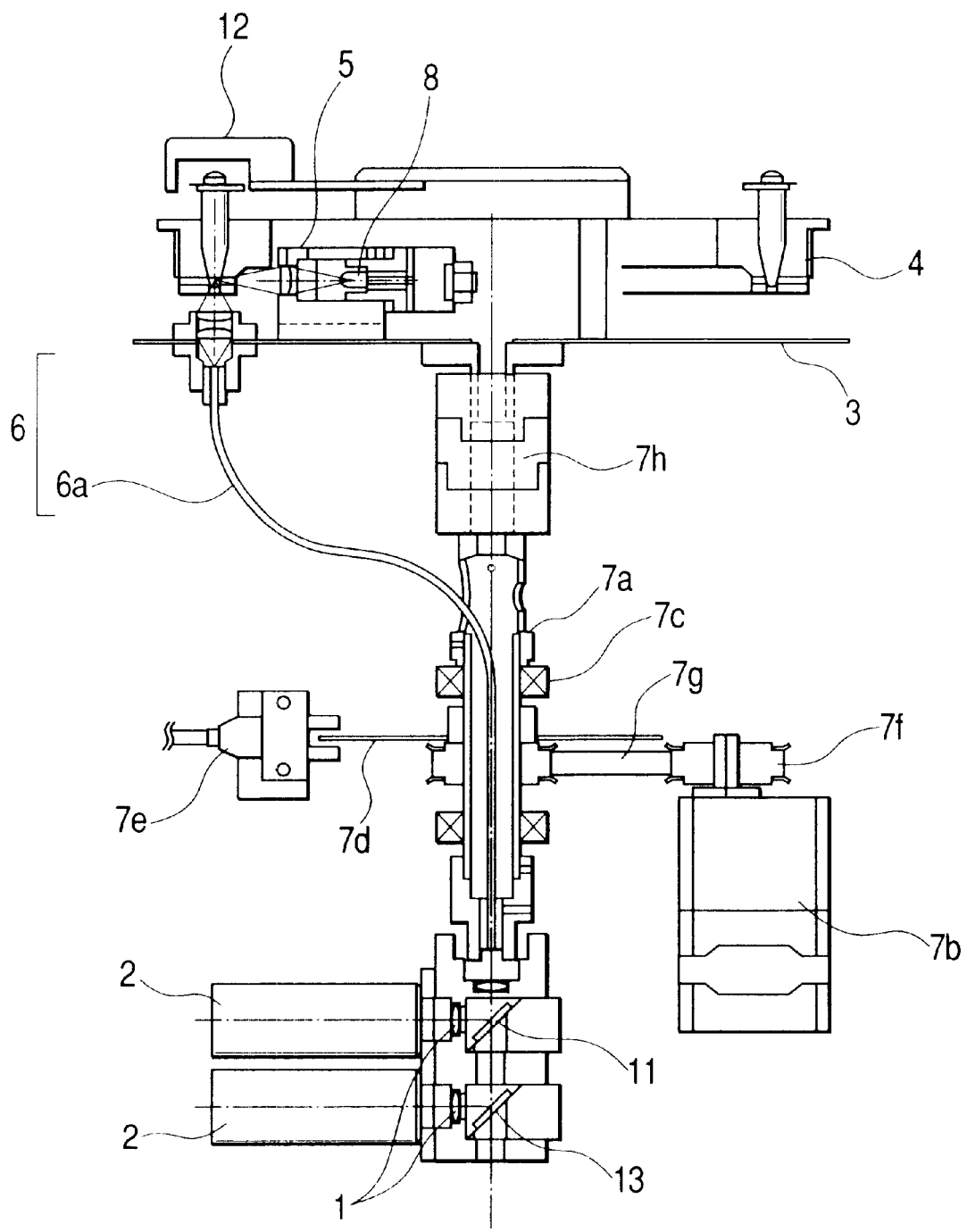
FIG. 8 is a front view to describe in detail a part of the fluorescence detection apparatus shown in FIGS. 7A, B.

FIGS. 4A and 4B show an outline of a fourth embodiment of the present invention, a fluorescence detection apparatus provided with an incubation function of temperature control means, useful for monitoring a large number of fixed samples in real time. That is, the fluorescence detection apparatus in FIGS. 4A, 4B is provided by adding temperature adjustment means (9) for controlling each sample at a predetermined temperature to the optical system of fluorescence analysis previously described with reference to FIGS. 1A and 1B.

The temperature adjustment means (9) for controlling each sample at a predetermined temperature uses one heater (9a) and one temperature sensor (9b). The top shape of a sample holder (4) is made annular, the heater (9a) is put on the outer periphery, and the temperature sensor (9b) is built in the sample holder (4), whereby each sample can be controlled at a predetermined temperature by thermal conduction from the sample holder (4).

Further, in the example in FIG. 4B, a heat insulation case (10) is placed for housing most of the sample holder (4), a partition plate (3), its rotation drive means, an excitation light source, excitation light optical means (5), and fluorescence optical means (6) fixed on the partition plate (3), and a shading plate (12). Preferably, the heat insulation case (10) is placed to shut off the sample temperature controlled by the temperature adjustment means from the outer temperature for enabling temperature adjustment with higher accuracy. Since the heat insulation case (10) is used for such a purpose, at least the sample holder may be housed in the heat insulation case (10).

Of course, the temperature adjustment means is not limited to the above-described method; for example, it is also possible to house at least the sample holder in a constant temperature tank at constant temperature and control by convection of air, etc. Further, the temperature adjustment means is not limited to heating of the heater, etc., and may be cooling or a heat cycle of repeating heating and cooling. To adopt cooling, a cooling element such as a Peltier device or a cooling fan may be used in place of the heater. To adopt the heat cycle, a heating element of a heater and a cooling element such as a Peltier device or a cooling fan may be used in combination.

The optical system of fluorescence analysis previously described with reference to FIGS. 1A, 1B and the sample temperature adjustment means are thus used in combination, whereby it is made possible to provide a fluorescence detection apparatus that can execute high-accuracy incubation at a predetermined temperature such as an enzyme reaction with a large number of samples and at the same time, monitors change of a fluorescence signal with time accompanying the enzyme reaction in real time.

To describe fluorescence detection apparatus of the invention in more detail, specific examples will be discussed with reference to FIGS. 7A to 10, but the invention is not limited to the specific examples.

FIGS. 7A to 10 are drawings to describe the fluorescence detection apparatus of the invention in detail.

Figure 9A:
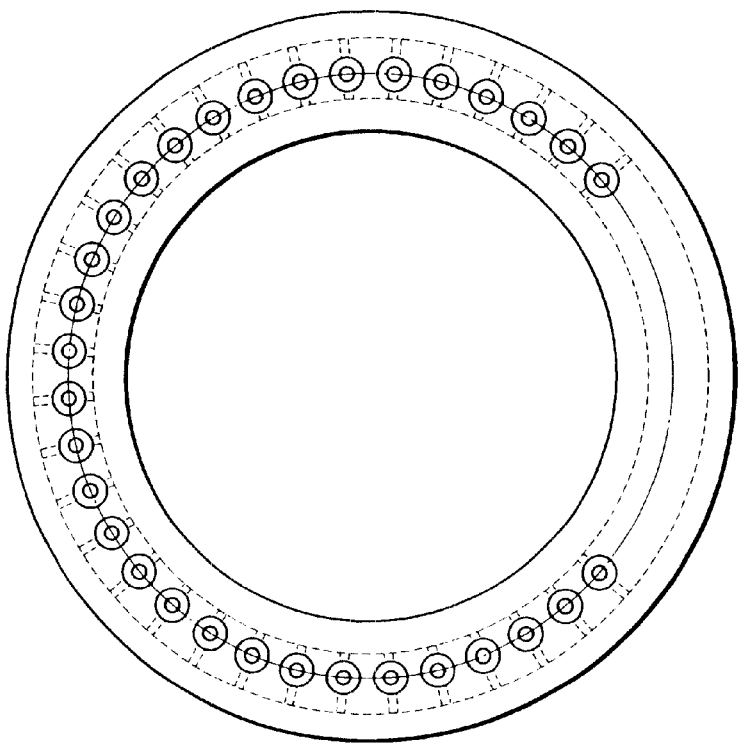
FIGS. 9A and 9B are respectively a top view and a front view to show the cross section to describe in detail a sample holder and temperature adjustment means of the fluorescence detection apparatus shown in FIGS. 7A, B.
Figure 9B:
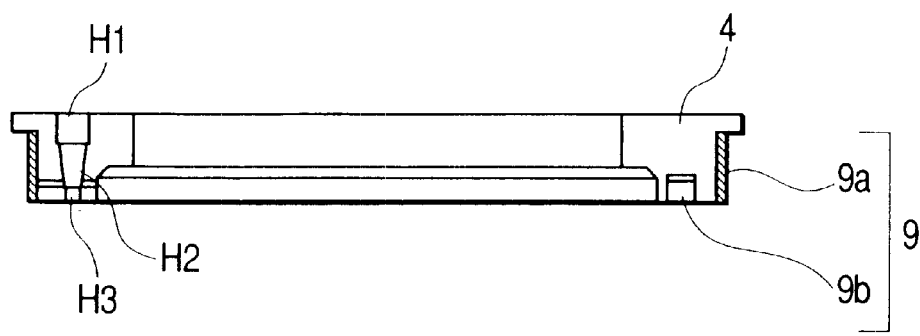
Figure 10:
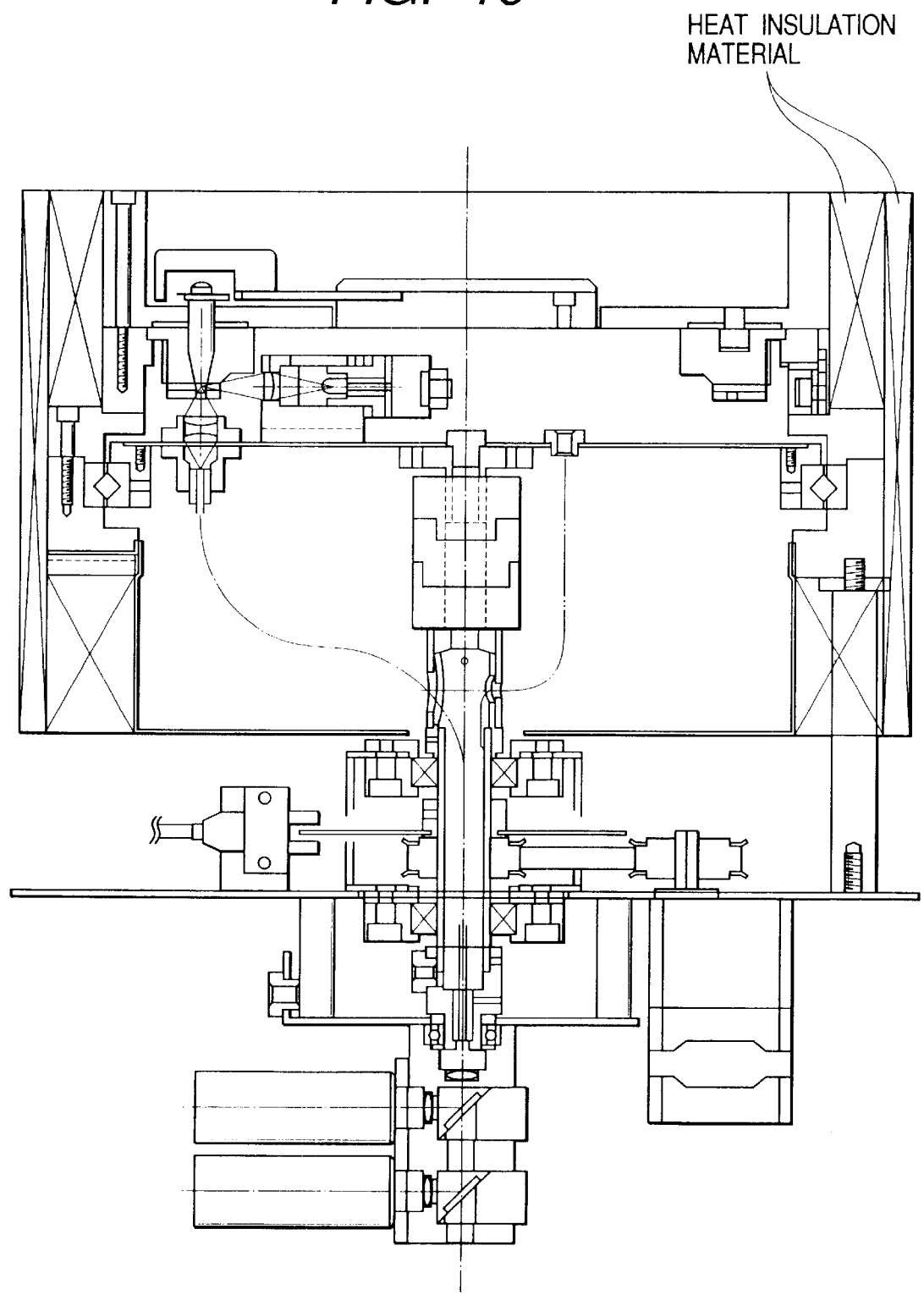
FIG. 10 is a front view to show the cross section to describe in detail a heat insulation case of temperature adjustment means, a part of the fluorescence detection apparatus shown in FIGS. 7A, B.

As shown in FIGS. 9A and 9B, sample holder (4) comprises an annular aluminum alloy part formed with 32 holes (H1) for inserting and holding sample vessels (S), 32 holes (H2) for allowing excitation light to pass through, and 32 holes (H3) for gathering fluorescence. As the holes for inserting and holding sample vessels, holes each fitted to the outer diameter of each sample vessel (maximum diameter φ8) are equally spaced from each other at 9-degree pitches on a circular arc 160 mm in diameter. The lower part of each hole is formed like a taper fitted to the sample vessel shape so as to be able to closely hold the bottom of the sample vessel. Each hole for allowing excitation light to pass through (φ2) is made so as to have the center axis made orthogonal to the center axis of the hole for inserting and holding a sample vessel (S). Further, each hole for gathering a fluorescence signal (φ3.4) is made in the bottom of the annular aluminum alloy part so as to have the center axis made the same as the center axis of the hole for inserting and holding a sample vessel.

A disk-like partition plate (3) is placed at a position approaching the sample vessels below the sample holder (4). Fixed on the partition plate (3) are a light emitting diode (light emission center wavelength 470 nm) as an excitation light source (8) and an interference filter for wavelength selection (transmission center 470 nm, half width 10 nm) and an optical lens for condensing as excitation light optical means (5). Further, a hole for allowing a fluorescence signal to pass through at a position at a distance of 80 mm from the center on the outer periphery of the partition plate (3), two condensing lenses for condensing fluorescence, and a light guide (6a) described later are fixed as fluorescence optical means (6). Further, a shading plate (12) is fixed for the purpose of preventing extraneous light from entering the sample vessel or the fluorescence optical means (6) under fluorescence measurement. The excitation light optical means (5) and the fluorescence optical means (6) are placed at positions such that their center axes are orthogonal to each other, whereby fluorescence induced by excitation light can be gathered efficiently.

A plastic optical fiber (φ2) is used as the light guide (6a) for communicating a fluorescence signal, a component of the fluorescence optical means (6). The fluorescence signal incidence end of the light guide (6a) is fixed below the partition plate (3) at the condensing point of the condensing lens. Further, the light guide is fixed to a rotation center axis so that the fluorescence signal emission end is positioned on the rotation center axis via the inside of the cylindrical rotation axis (7a) of rotation drive means (7) of the partition plate (3) described below.

Further, drive means (7) comprising: cylindrical rotation axis (7a); a stepping motor (7b); a bearing (7c); a rotation slit (7d); a rotation position sensor (7e); a timing pulley (7f); a timing belt (7g); and a coupling (7h) being joined to the partition plate (3). Thus, the partition plate (3) and the excitation light source (8), the excitation light optical means (5), the fluorescence optical means (6), and the shading plate (12) fixed to the partition plate (3) are rotated integrally in response to the operation of the drive means (7).

The rotation slit (7d) and the rotation position sensor (7e) are provided, whereby it is also made possible to detect the state of rotation of the partition plate (3), namely, the position of the sample vessel where fluorescence is detected at each instant.

A dichroic mirror as wavelength dispersion means (11) is placed ahead the fluorescence signal emission end of the light guide (6a) with an optical lens between for optical path division according to the wavelength with about 560 nm as the boundary. An optical filter for wavelength selection (interference filter; 520 nm), an optical lens, and a photosensor (photomultiplier tube) are placed on the optical path of reflected light (560 nm or less) by the dichroic mirror. On the other hand, a total reflection mirror, an optical filter for wavelength selection (interference filter; 610 nm), an optical lens, and a photosensor (photomultiplier tube) are placed on the optical path of transmitted light (560 nm or more) by the dichroic mirror. Thus, fluorescence signals having wavelengths of 520 nm and 610 nm are detected at the same time.

The described parts are designed and assembled so that their positional relationships are defined by a base plate, a support ring, a column, etc.

Further, a heater (9a) is put on the outer periphery of the sample holder (4) and a temperature sensor (9b) is installed in the sample holder (4). A tape heater is used as the heater (9a) and a platinum temperature-measuring resistor is used as the temperature sensor (9b). Further, the sample holder, the partition plate, some parts of the rotation drive means, the excitation light source, the excitation light optical means, and the fluorescence optical means are housed in a heat insulation case. The heat insulation case is formed of a material of small thermal conductivity such as polyacetal-family plastic or expanded polyethylene. Thus, heat is shut off from the outside, the temperature of each sample is controlled with high accuracy, and an incubation function of an enzyme reaction, etc., is provided.

The described fluorescence detection apparatus detects a fluorescence signal of each sample as follows: Excitation light emitted from the light emitting diode excites a sample in a sample vessel inserted into and held in the sample holder through the excitation light optical means. Fluorescence produced by the sample is emitted from the lower part of the sample holder and is communicated via the fluorescence optical means of the light guide, etc., placed on the partition plate. The fluorescence communicated along the light guide is dispersed into optical paths by the wavelength dispersion means and reflected light and transmitted light are selected according to the wavelength through the interference filters of 520 nm and 610 nm respectively, then converted into electric signals by the photomultiplier tubes and detected.

Since the 32 sample vessels are fixedly placed on the circular arc, excitation with excitation light and fluorescence gathering by the fluorescence optical means are executed in order as the partition plate is rotated. This means that fluorescence detection can be easily accomplished about a large number of samples (in the example, 32 samples). After termination of fluorescence measurement of 32 samples, the partition plate is rotated reversely for once restoring the rotation position to the former position and the above-described operation is repeated, whereby change of a fluorescence signal with time for each sample can be monitored intermittently.

According to the fluorescence detection apparatus of the invention, the following advantages can be provided:

Since the sample holder capable of holding a plurality of sample vessels is fixedly placed, high-accuracy temperature adjustment can be made for each of the samples stored in the sample vessels, whereby a large number of samples can be treated promptly. Moreover, the sample vessels are fixedly placed and are not transported, so that the risk of occurrence of a temperature difference between the samples during transporting or occurrence of carry-over caused by vibration or swing at the transporting time can also be excluded.

If the temperature adjustment means is provided, the photosensor can be placed outside the temperature adjustment means, so that a noise rise accompanying a temperature rise does not occur and high-sensitivity signal detection can be made. Moreover, only one photosensor is used per wavelength, thus costs can be reduced and at the same time, the apparatus can be miniaturized and intricate work of sensitivity correction of each photosensor required for using a plurality of photosensors per wavelength can also be skipped. Further, since change of fluorescence signals of a large number of samples with time can be known simply by processing the signal from one photosensor per wavelength, the load involved in data processing is also light. Particularly, if photomultiplier tubes are preferably adopted as the photosensors, an extremely high-sensitivity fluorescence detection apparatus can be provided. According to the configuration of the fluorescence detection apparatus, sufficient sensitivity to a feeble fluorescence signal can also be provided.

Since the light guide is fixedly placed on the partition plate and is rotated holding the same form, the bend state of the light guide does not change at all. Therefore, there is no change in light communication efficiency accompanying change in the bend state of each optical fiber; consequently, signal detection good in reproducibility can be made.

In the apparatus of the invention, the mechanical move parts are limited only to the partition plate and the parts fixed thereto and moreover only simple rotation is executed. Thus, mechanical trouble can be minimized. Thus, in the invention, real-time monitoring of a large number of samples is accomplished by rotating the partition plate and the optical means although the sample vessels are not transported or moved at all.

The problem of insufficient sensitivity arising when a small-sized and low-output excitation light source is used in the apparatus as shown in FIG. 5A to 6B can also be solved by using one light guide as the fluorescence signal communication means. In fact, in the above-described embodiments, the effective output of the light emitting diode used as the excitation light source is only $1/40$ that of the argon ion laser used with the apparatus as shown in FIGS. 5A to 6B. However, fluorescence detection disclosed in the present invention can be realized with sensitivity equal to that provided by the apparatus as shown in FIGS. 5A to 6B. Since the ring-type light guide is not used, the costs can also be reduced.

As described above, the invention provides the fluorescence detection apparatus that can monitor a fluorescence signal in real time while incubating each sample at a predetermined temperature, satisfying the requirements of (a) high-accuracy temperature adjustment, (b) rapid treatment of a large number of samples, (c) high sensitivity, (d) high reliability (decrease in mechanical trouble, improvement in reproducibility of fluorescence detection, decrease in the risk of carry-over), (e) low costs (simplification of apparatus configuration, use of no expensive parts in data processing, etc.,), (f) miniaturization of the apparatus, and the like.

What is claimed is:

1. A fluorescence detection apparatus comprising:
   a sample holder for fixing and holding a plurality of vessels on a circular arc;
   a driving unit;
   a partition plate for rotating integrally by being joined to said driving unit;
   an excitation light source coupled to said partition plate;
   an excitation light optical unit;
   a fluorescence optical unit being fixed on said partition plate for rotation integrally; and
   at least one photosensor for detecting a fluorescence signal from each of samples in the sample vessels,
   wherein said partition plate comprises a passing portion for allowing the fluorescence signal through passing from the sample vessels,
   wherein said photosensor is mechanically discontinued from said drive unit and fixedly placed,
   wherein said excitation light optical unit is placed so as to selectively excite one of the sample vessels in order, corresponding to the rotation of the partition plate,
   wherein said fluorescence optical unit includes a light guide for communicating the fluorescence signal from the sample vessel to said photosensor, and an incidence end of said light guide is placed facing said passing portion and an emission end of said light guide is placed on a center axis of the rotation facing said photosensor.

2. The fluorescence detection apparatus as claimed in claim 1 further including wavelength dispersion unit facing the emission end of the light guide for dispersing fluorescence into optical paths based on the wavelength of the fluorescence signal,
   wherein photosensor is fixedly placed on each of the dispersed optical paths.

3. The fluorescence detection apparatus as claimed in claim 1, further including a shading plate for covering at least the top of one sample vessel, said shading plate being fixed to said partition plate so as to be positioned above the fluorescence incidence end of the light guide, wherein the shading plate is rotated with said partition plate integrally.

4. The fluorescence detection apparatus as claimed in claim 1, wherein at least one of a light emitting diode or a semiconductor laser is used as said excitation light source.

5. The fluorescence detection apparatus as claimed in claim 1, wherein said light guide is at least one optical fiber.

6. The fluorescence detection apparatus as claimed in claim 2, wherein said wavelength dispersion unit is a dichroic mirror.

7. The fluorescence detection apparatus as claimed in claim 2, wherein said wavelength dispersion unit is a diffraction grating.

8. The fluorescence detection apparatus as claimed in claim 1, further including temperature adjustment unit for controlling each sample at a predetermined temperature.

* * * * *